United States Patent
Zabicky et al.

(10) Patent No.: US 8,377,469 B2
(45) Date of Patent: Feb. 19, 2013

(54) NANO- AND MESOSIZED PARTICLES COMPRISING AN INORGANIC CORE, PROCESS AND APPLICATIONS THEREOF

(75) Inventors: Jacob Zabicky, Beer Sheva (IL); Charles Linder, Rehovot (IL); Sarina Grinberg, Meitar (IL); Eliahu Heldman, Rehovot (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 1044 days.

(21) Appl. No.: 11/813,311

(22) PCT Filed: Jan. 2, 2006

(86) PCT No.: PCT/IL2006/000009
§ 371 (c)(1),
(2), (4) Date: Aug. 11, 2008

(87) PCT Pub. No.: WO2006/072943
PCT Pub. Date: Jul. 13, 2006

(65) Prior Publication Data
US 2009/0011002 A1    Jan. 8, 2009

Related U.S. Application Data

(60) Provisional application No. 60/640,218, filed on Jan. 3, 2005.

(51) Int. Cl.
*A61K 9/127* (2006.01)
(52) U.S. Cl. .......................... 424/450; 264/4.1; 264/4.3
(58) Field of Classification Search ............... 424/450
See application file for complete search history.

(56) References Cited

U.S. PATENT DOCUMENTS

| | | | | | |
|---|---|---|---|---|---|
| 1,937,661 | A | * | 12/1933 | Meyer | 423/46 |
| 1,943,338 | A | * | 1/1934 | Mitchell | 423/96 |
| 4,839,111 | A | * | 6/1989 | Huang | 264/4.6 |
| 6,369,206 | B1 | | 4/2002 | Leone et al. | |
| 2003/0113369 | A1 | * | 6/2003 | Martin et al. | 424/450 |
| 2007/0231393 | A1 | * | 10/2007 | Ritter et al. | 424/489 |
| 2008/0063898 | A1 | * | 3/2008 | Lally et al. | 428/688 |

* cited by examiner

*Primary Examiner* — Gollamudi Kishore
(74) *Attorney, Agent, or Firm* — Klauber & Jackson LLC

(57) ABSTRACT

Method for the preparation of nano- and mesosized particles consisting of a lipid layer comprising at least one amphiphile and a core of an inorganic compound and/or a metal, comprising: (i) dissolving in a common solvent at least one self-aggregating amphiphile with at least one inorganic, organometallic or metallorganic precursor of said inorganic compound or metal; and (ii) either injecting the resulting solution into an aqueous solution or drying the resulting solution and re-hydrating it, so as to form particles in which the precursor is encapsulated by the amphiphile(s) and is converted therein to said inorganic compound and/or metallic solid form.

17 Claims, No Drawings

NANO- AND MESOSIZED PARTICLES COMPRISING AN INORGANIC CORE, PROCESS AND APPLICATIONS THEREOF

FIELD OF THE INVENTION

The present invention relates to nano- and mesosized particles comprising an inorganic core, their manufacturing process and applications thereof.

BACKGROUND OF THE INVENTION

Liposomes can be used as templates to direct the formation of inorganic structures. Hentze et al. (2003) describe a procedure to form hollow silica particles of 60 to 120 nm diameter by first forming vesicles and addition of an inorganic precursor to silica to this vesicle dispersion. The vesicles act as templates for the directed growth of silica on their surface. In this way, hollow silica particles were formed with about a 2 nm-thick shell and with a core diameter identical to that of the template. Either discrete hollow particles or networks of linked or aggregated particles can be formed.

Liposomes and vesicles are further used to form multilamellar inorganic shells by first forming a multilamellar liposome or vesicle and then adding to the solution an inorganic precursor that does not hydrolyze rapidly in water, such as TEOS (tetraethyl orthosilicate). This precursor then accumulates between the lipophilic lipid layers, where it polymerizes and crosslinks to form a solid insoluble multilamellar inorganic multilamellar shell. The liposome or vesicles amphiphiles may be subsequently removed. For example, Tanevt and Pinnavaia (1998) described an approach to direct biomimetic assembly of lamellar silicas. The approach is based on the hydrolysis and condensation of a neutral silicon alkoxide precursor such as TEOS in the multilamellar regions of vesicle structure made from a neutral diamine bola-amphiphile. The bola-amphiphile acts as a neutral diamine template to form a framework for the precursor but also acts as a multilamellar vesicle-type nanoreactor governing the direction of framework growth and the particle architecture. In this approach, the multilamellar vesicle is first formed; then, an inorganic precursor that does not hydrolyze rapidly (e.g., TEOS) is added to the external solution, from which it diffuses into the spaces between the lamella and polymerizes therein.

Jung et al. (2000) disclosed the use of two different diaza-crown-appended cholesterol gelators for solvent gelation. For example, one derivative was added to a solution containing aniline, water and TEOS and warmed and then cooled to form a gel. The gel formed contained linearly linked spherical meso- to micron-sized vesicles of 200 to 2000 nm diameter, wherein the linearly linked small vesicles caused the gelation. In effect, the spherical vesicle structures of organogels were formed into silica structures by the sol-gel polymerization of TEOS in the gel phase, wherein the spherical silica obtained in the acidic conditions consists of multilayered vesicle structure.

Kiatagiri et al., 2003, disclose a class of nano hybrid materials, called by the authors "Cerasome", bearing a liposomal bilayer structure and surface, wherein by a sol-gel reaction a double chain proamphiphile having a trialkoxysilane as the head moiety self-assembles into a bilayer vesicle. The silica precursor then reacts to polymerize and crosslink resulting in vesicles comprised of silica shells. Other head group moieties can be used such that surface modification of the Cerasome with amino groups is achieved by replacing TEOS with 3-aminopropyl-triethoxysilane.

Amphiphiles have also been used to coat preformed inorganic particles. U.S. Pat. No. 5,441,746 discloses an electromagnetic wave-absorbing surface modified magnetic particles for use in medical applications. The magnetic particles are coated with an amphipathic organic compound and an amphipathic vesicle-forming lipid. These particles may be used in treatment of cancer and infectious diseases. In one approach, the wave absorbing magnetic core liposome is first coated with an amphipathic organic compound, which contains both a hydrophilic and hydrophobic moiety. For example, fatty acids, such as oleic acid, linoleic acid or linolenic acid, dispersed in an organic solvent, are directly added to the preformed particles. The coated particles are then dispersed in an organic solvent and then coated with a vesicle-forming lipid such as phosphatidylcholine, phosphatidic acid, phosphatidylinositol, phosphatidyl ethanolamine (PE), sphingomyelin and glyco-lipids, such as cerebroside and gangliosides. The coated particles comprise ferrite or mixed ferrite materials, preferably of a uniform, controllable size and narrow size distribution, wherein the primary component, the oxide, is of the formula $M_2^{(+3)}M^{(+2)}O_4$, wherein $M^{(+3)}$ is Al, Cr or Fe, and $M^{(+2)}$ is Fe, Ni, Co, Zn, Zr, Sr, Ca, Ba, Mg, Ga, Gd, Mn or Cd, and the oxides can be mixed with LiO, CdO, NiO, FeO, ZnO, NaO, KO and mixtures thereof. The targeted wave absorbing magnetic core liposome may be prepared to include ferrites useful as cancer chemotherapeutic agents. In one method of synthesis, the magnetic core liposomes are prepared to include PEG-PE and PG on the liposome backbone to aid in targeting to specific areas and to avoid reticuloendothelial system (RES) uptake.

In a similar approach, disclosed in U.S. Pat. No. 5,389,377, liposomes are provided containing a solid inorganic core consisting of metals and metal oxides of Fe, Co, Ni, Zn, Mn, Mg, Ca, Ba, Sr, Cd, Hg, Al, B, Sc, Ga, V, In, and mixtures thereof, coated with a first amphipathic organic compound and further coated with a second amphipathic vesicle forming lipid. The cores may be $Fe_3O_4$, $Fe_2O_3$, $Al_2O_3$, $TiO_2$, ZnO, FeO, and Fe or mixtures thereof, the first amphipathic organic compound is preferably a fatty acid and the second amphipathic organic is preferably is a phospholipid or a glycolipid or mixtures thereof.

In US Patent Application 2002/0103517, nano-sized shells made from metals such as gold, silver, copper, platinum, palladium, lead, and iron, are housed within a liposome and the specific binding ligand is functionally incorporated into a liposome membrane. Gold is most preferred. Gold nano shells possess physical properties similar to gold colloid, in particular, a strong optical absorption due to the collective electronic response of the metal to light and are more amenable to a directed shift in their plasmon resonance and hence absorption or scattering wavelengths than the solid metal nanoparticles. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit up regulation of the EGF receptor.

All the above approaches are based on first forming either the core nano-particle and then coating them with amphiphilic derivatives or first forming the liposome or vesicle and using them as a template to form an inorganic shell or the formation of a gel from the addition of amphiphiles to an organic solution, which forms structures inside the gel which are used to form inorganic particles.

In the use of amphiphiles to coat previously made particles, the role of the amphiphile is not to control or template the final inorganic particle, but rather to modify its existing surface properties. In all cases, the amphiphile and the inorganic precursor are not initially an intimate mixture in a common solvent. As a result, a given equilibrium for an equilibrium distribution of the solid inorganic precursor must occur. Thus, all these approaches for using templates of amphiphile aggregates and adding the precursors to the solutions containing the vesicles or liposomes, are difficult to control, the final product characteristics may require multiple steps, and the final product exhibits a certain lack of homogeneity. In addition, in the examples requiring the distribution of an inorganic precursor between the lamella of a vesicle or liposome, or in the procedure wherein the inorganic precursor is first in contact with water, then only compounds that undergo relatively slow reactions with water can be used as the compound must first form an equilibrium distribution within the amphiphilic structures before reacting to form a solid Thus, in many of the examples cited in the state of art, slow reacting tetraethyl orthosilicate (TEOS) is used and the use of faster reacting precursors such as titanum and zirconium alkoxides or similar derivatives cannot be used because of their rapid reactions within water.

SUMMARY OF THE INVENTION

It has now been surprisingly found, in accordance with the present invention, a simple and more general method whereby an amphiphile and a precursor that may be an inorganic-organic compound, metallo-organic compound, a metal complex or a metal chelate, are dissolved in a common non-reacting solvent, the solution mixture is exposed to an aqueous solvent whereby the amphiphile self-aggregates and forms vesicles or liposomes, and the precursor is first encapsulated within the vesicle or liposome where it undergoes a reaction to form a solid particle encapsulated within the vesicle or liposome.

The present invention thus relates to a method for the preparation of nano- and mesosized particles consisting of a lipid layer comprising at least one amphiphile and a core of an inorganic compound and/or a metal, said method comprising:

(i) dissolving in a common solvent at least one self-aggregating amphiphile with at least one inorganic, organometallic or metallorganic precursor of said inorganic compound or metal; and (ii) either injecting the resulting solution into an aqueous solution or drying the resulting solution and re-hydrating it, so as to form in both cases nano- and mesosized particles in which the precursor is encapsulated by the amphiphile(s) and is converted therein to said inorganic compound and/or metallic solid form.

The nano- and mesosized particles of the invention may be vesicles, liposomes or tubular particles. The term "mesosized" as used herein includes both submicron- and micron-sized particles. The term "precursor" as used herein denotes the least one inorganic, organometallic or metallorganic precursor of the solid inorganic compound and/or metal that constitute the core of the particles obtained by the method of the invention. It should be understood herein that the core may still contain some residual components selected from the precursor(s) and/or components added to the solution after initial vesicle formation step.

DETAILED DESCRIPTION OF THE INVENTION

The present invention relates to a method for forming nano- and mesosized particles containing an envelope of amphiphilic derivatives and an inorganic compound or metal core, said method comprising dissolving one or more amphiphilic derivatives that can form vesicles/liposomes and an inorganic compound or metal precursor in a common solvent or solvent combination, drying the mixture or solution and adding it, or exposing it simultaneously, to a water solution or aqueous solvent in which the inorganic or metal precursor is relatively non-stable, thus forming hybrid organic-inorganic vesicles in which the amphiphilic derivatives encapsulate the inorganic or metal precursor core.

As used herein, "common solvent" refers to a solvent or combination of solvents in which both the amphiphile and the precursor dissolve and no reaction occurs between them. The inorganic or metal precursor should be relatively stable with respect to the solvent(s) and the amphiphile(s) used.

In one embodiment, the common solvent is an alkanol such as ethanol or isopropyl alcohol, and the method consists in injecting the alcoholic solution comprising the amphiphile and the precursor under the surface of an aqueous solvent, whereby the amphiphile forms vesicles or liposomes and wherein, within the encapsulated space of the vesicle or liposome, the inorganic, organometallic, or metallorganic compound or metal complex reacts with the water to form water-insoluble nano- or mesosized-particles encapsulated within said vesicle or liposome. Typically, this can be achieved by injection of an alcoholic solution through a small bore Hamilton syringe into a well-stirred aqueous solution. The solvent, i.e., ethanol, can then be removed. This method, called 'ethanol injection', was first described by Batzri and Korn (1973). In addition to ethanol and isopropyl alcohol, other water-soluble alcohols and water-miscible solvents such as tetrahydrofuran (THF), N-methylpyrrolidone (NMP), dimethylformamide (DMF) and dimethyl sulfoxide (DMSO), or a combination thereof, may be used. The solvent may be removed at a later stage by evaporation or dialysis or by centrifugation of the particles and re-dispersion, or by any other technique well known in the art.

In another embodiment, the common solvent is not water-miscible and undergoes evaporation after its addition or injection into the water. Such solvents are ethers, e.g., alkyl ethers, arenes, chlorinated hydrocarbons, chlorofluorinated, fluorinated and perfluorinated hydrocarbons. The boiling points are preferably less than 200° C., more preferably less than 120° C. and most preferred less than 100° C. Preferred solvents are diethyl ether, methylene chloride, chloroform and toluene. After addition to the water, the solvent is evaporated by heating or by stirring at room temperature. In one preferred mode, the solution is added or injected to a stirring preheated water solution and the rate of addition, the temperature and the stirring are such that the solvent evaporates at approximately the same rate at which it is added. In such a process the preferred solvents are low boiling point solvents such as diethyl ether. The approach of injection of an immiscible organic solvent into water followed by evaporation of the solvent is described for liposome formation in Deamer, 1978.

In another method that can be used in accordance with the invention, the organic phase is removed under reduced pressure. In this case, the organometallic compound or organometallic complex is chosen to be soluble in the organic solvent or solvent mixtures as is the amphiphile, which promotes vesicle formation.

Another method of forming the nanoparticles of this invention is the so-called film formation-hydration and sonication. In this process, a film resulting from evaporating a solution containing the precursor(s) is subjected to sonication in the presence of an aqueous dispersing medium, resulting in the spontaneous formation of liposomes or vesicles containing the precursor.

In all the above cases, the composition of the aqueous solution may be adjusted with respect to pH, the presence of reducing or oxidation agents, and salts or complexants in order to enhance or direct the conversion of the precursor into its final insoluble form.

In general, any vesicle-forming method can be used in the invention if the amphiphilic derivatives forming the vesicles can be mixed with the inorganic or metal precursor in a solvent or solvent combination in which said precursors are relatively stable and this mixture or solution is added or exposed simultaneously to the water solution or solvent in which the inorganic or metal precursor is relatively non-stable and forms an insoluble material and in which the amphiphilic derivatives form vesicles.

The vesicles may undergo further treatment after their formation such as thermal or chemical, e.g. oxidation or reduction, treatment.

As mentioned above, the formed vesicles or liposomes encapsulate the precursor. When core of an inorganic compound is desired, it is retrieved from the precursor by hydrolysis and, when necessary, exposure to a chalcogenic reagent. When a metallic core it desired, it is, produced by reduction from the metal precursor by adding a reducing agent to the aqueous solution or by photochemical means.

The at least one amphiphile for use in the method of the present invention is chosen from compounds which for monolayer, bilayer or multilamellar vesicles or liposomes.

In one embodiment, the amphiphile is a symmetric or asymmetric bolaamphiphile that forms monolayer vesicles or liposomes. Bolaamphiphiles are double-headed amphiphiles in which hydrophilic groups at each end are connected by hydrophobic functionalities, and which are able to form a monolayer lipid membrane (ELM). When the bolaamphiphiles are unsymmetrical, with two headgroups of different size, the resulting MLMs are classified into two categories—unsymmetrical or symmetrical, depending on a parallel or antiparallel molecular packing with the layer, respectively. Both symmetric and asymmetric bolaamphiphile structures may give vesicles. There are also many examples of bolaamphiphiles, which do not form spherical vesicles unless cholesterol or another additive, which can give curvature, is added to the formulation. There are also examples of bolaamphiphiles, which do not form spherical vesicles under any condition. Some symmetric and asymmetric bolaamphiphiles only form spherical vesicles when molecular structures are present to prevent the formation of fibers, tubules, ribbons, etc. Examples of bolaamphiphiles that can be used in the present invention are the symmetric and asymmetric bolaamphiphiles derived from vernonia oil, castor oil or lesquerrella oil, described in the PCT Publications WO 03/047499 and WO 02/055011, of the same applicant. The following references on bolaamphiphiles are incorporated herein by reference in their entirety: Schnur 1993; Fuhrhop and Helfrich, 1993; Fuhrhop and Wang, 2004; WO 03/047499; WO 02/055011; and US Patent Application 2002/0137233 A1.

In another embodiment, the at least one amphiphile is an amphiphile containing one or more chains and one or more headgroups with a packing geometry that allows formation of bilayer or multilamellar vesicles or liposomes. Such an amphiphile may contain 1, 2, 3 or more chains and 1, 2, 3 or more headgroups and may be an anionic, cationic, zwitterionic or neutral lipid.

Examples of zwitterionic lipids that can be used according to the invention are phospholipids such as phosphatidylcholine (PC), phosphatidylethanolamine (PE), sphingomyelin, and the like.

Anionic amphiphilic lipids that can be used in the invention include phospholipids such as phosphatidylglycerol, phosphatidylserine, phosphatidyl-inositols, phosphatidic acid, and fatty acid esters thereof, wherein the fatty acid moiety has 10-24, more preferably 16-18, carbon atoms, and non-phospholipid amphiphiles such as saturated or mono- or polyunsaturated free fatty acids of 10-24, more preferably 16-18, carbon atoms, and esters and amides thereof. The fatty acids include preferably palmitic acid, stearic acid, arachidonic acid, oleic acid, linolenic acid, linoleic acid, and myristic acid, and the amides include anandamides and methanandamides.

In another embodiment, the charged lipids used in the invention carry a net positive charge at pH 7, and the lipid is a cationic lipid. Cationic lipids which may be used in the present invention include stearylamine, quaternary ammonium compounds with at least two long aliphatic chains such as dimethyldioctadecyl-ammonium bromide, diacyloxy di- and trimethyl ammonium propane and diacyloxy di- and triethylammonium propane (wherein the acyl has 10-24, more preferably 16-18, carbon atoms), for example, N-[1-(2,3-dioleoyloxy)propyl]-N,N,N-trimethyl-ammonium chloride, and diacyl dimethylammonium propane stearylamines. Additionally, a wide array of synthetic cationic lipids can function in the present invention. These include common natural lipids derivatized to contain one or more basic functional groups.

Preferred phospholipids for use in the invention are phosphatidylcholine (PC) diacyl esters with saturated or unsaturated fatty acids or with aromatic acids such as, but not limited to, dioleoyl-PC, dimyristoyl-PC (DMPC), dipalmitoyl-PC, distearoyl-PC (DSPC), diarachidonyl-PC (DAPC), and diphthaloyl-PC (DPPC); phosphatidylethanolamine (PE) diacyl esters with saturated or unsaturated fatty acids or with aromatic acids such as, but not limited to, dioleoyl-PE, dimyristoyl-PE (DMPE), dipalmitoyl-PE (DPPE) and distearoyl-PE (DSPE); phosphatidylserine; phosphatidylglycerols, including distearoylphosphatidylglycerol (DSPG); phosphatidylinositol; phosphatidic acids (PA) such as dipalmitoyl-PA (DPPA) and distearoyl-PA (DSPA).

In one embodiment, the anionic or cationic lipid is fluorinated. Any of the anionic or cationic lipids described hereinabove may be fluorinated by replacing at least one hydrogen atom with a fluorine atom. One skilled in the art will recognize that countless other natural and synthetic variants carrying negative charged moieties will also function in the invention.

Also suitable for use in the present invention are the synthetic lipids described in U.S. Pat. No. 5,312,617, the disclosure of which is hereby incorporated by reference herein in its entirety, and lipid-bearing polymers such as chitin, hyaluronic acid, polyvinylpyrrolidone or polyethylene glycol (PEG), also referred to herein as "pegylated lipids" with preferred lipid-bearing polymers including pegylated DPPE (DPPE-PEG), which refers to the lipid DPPE having a PEG polymer, e.g., of molecular weight 5000 Da, attached thereto.

Another class of amphiphilic derivatives, which are used in preferred embodiments of the present invention, are the amphiphilic derivatives derived from vernonia, castor or lesquerella oils disclosed in WO 03/04749 and WO 02/055011 of the same applicant, herein incorporated by reference as if fully disclosed herein. The amphiphilic derivatives suitable for the present invention are bolaamphiphiles, single headed amphiphiles with one or two or three hydrophobic chains or triheaded or diheaded amphiphiles with two or three aliphatic chains. In one preferred case, the chains are united by a glycerol backbone. Preferred amphiphiles are derived from vernonia oil, and more preferred is N,N'-ethylene-bis(vernolamide) prepared from the methyl ester of octadec-9-en-12(13)-hydroxy, 13(12)-oxycarbonyl-N-methylene-N,N-dimethyl-N-dodecylammonium chloride (disclosed as Derivative 2 in Example 5 of WO 02/055011), of the structure:

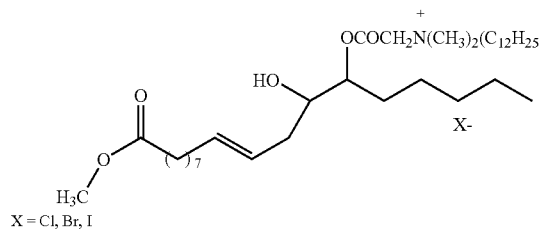

X = Cl, Br, I and the quaternary amphiphilic vernonia oil derivative herein designated VO quat DMDoA Cl (disclosed as Derivative 23 in Example 34 of WO 02/055011), of the structure:

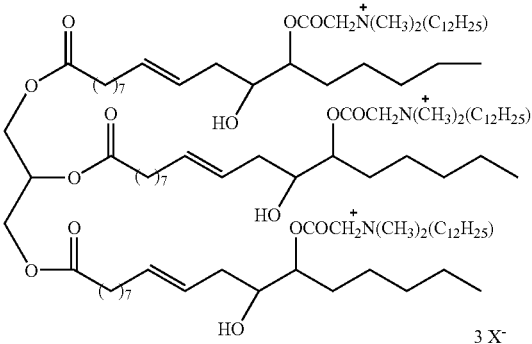

Thus, according to the present invention, non-limiting examples of the amphiphiles that can be used in the invention include: anionic lipids such as phospholipids, free saturated or unsaturated fatty acids and esters or amides thereof; cationic lipids such as phospholipids, diacyloxy trialkylammonium propanes, and quaternary ammonium compounds containing at least two long aliphatic chains; and zwitterionic lipids such as phospholipids.

According to one embodiment of the invention, the at least one amphiphile is a combination of two amphiphiles in which one forms monolayer and the other forms bilayer or multilamellar vesicles or liposomes.

Different types of vesicles can be obtained according to the present invention. One type is a bilayer vesicle formed from double-chain diacyl amphiphiles. These chains may be made from phospholipids or from non-phosphorous containing amphiphiles. Another type is a bilayer vesicle formed from single-chain amphiphiles comprising a polar head group, then a flexible chain, a rigid segment (consisting of benzene rings such as biphenyl, diphenylazomethine, azobenzene and other groups known in the art) and finally a relatively long flexible chain (Kunitake et al., 1981). A further type is a bilayer vesicle made from triple-chain amphiphiles containing two ionic head groups (see as an example Sumida et al., 2001), and vesicles made from triple chain amphiphiles containing three polar head groups on the same side. An additional type is a vesicle made from a mixture of amphiphiles with dissimilar aliphatic chains and/or dissimilar head groups, such that one will form bilayers and the other will form bilayer domains or monolayer domains of the second amphiphile.

In another embodiment of the invention, the amphiphile does not have the packing geometry that allows formation of bilayer or multilamellar vesicles or liposomes and this ability can be provided by several agents or means such as (i) addition of cholesterol or a cholesterol derivative; or (ii) addition of an additional amphiphile that imparts to the first amphiphile the capability of formation of bilayer or multilamellar vesicles or liposomes.

The amphiphile may further contain polymerizable or reactive groups which, after vesicle or liposome formation, may undergo polymerization and/or cross-linking.

Cholesterol and cholesterol derivatives, e.g. ethers or esters, can be used to strengthen the vesicles of the invention. In addition, modifications in the lipid chains may also improve the properties of the vesicles and liposomes. Lipids are chemically sensitive biomolecules and undergo different degradation reactions such as hydrolysis and oxidation. If the amphiphilic derivatives of the vesicles contain double or triple bonds, then their hydrogenated derivatives can be used to improve oxidation stability. In addition, ether rather than ester linkages in various parts of the amphiphilic molecules can be used and will be more chemically stable.

Materials, which can also be added as minor components to the vesicles of the invention to improve one or more properties, are amphiphilic derivatives taken from zwitterionic, acidic, or cationic lipids as defined above and, more preferably, phosphatidylcholine, phosphatidylethanolamine, sphingomyelin, phosphatidyl-glycerol, phosphatidylserine, phosphatidylinositols, phosphatidic acid, stearylamine, diacyloxy trimethylammonium propanes, diacyloxy dimethylammonium propanes. In addition, the liposomes and vesicle bilayers of the invention can be mechanically stabilized by polymerization or by fluorinated lipids to form stronger and less permeable barriers because of hydrophobic interactions.

The membranes coating the nanoparticles of the invention may optionally be crosslinked, a property that may be needed in certain applications.

The amphiphilic derivatives of the vesicles and liposomes can have reactive and polymerizable double or triple bonds and can form vesicle structures, and said amphipathic chains can be subsequently covalently bound to each other forming stable macromolecular structures. In addition, the head groups of the amphiphilic molecules, which if they contain polymerizable or condensable groups can also be reacted to modify surface property, fix the surface of the vesicles and liposomes. Furthermore, other amphiphilic derivatives having oligomeric or polymeric chain moieties can be added during the vesicle formation stage as a minor component, and have a major effect on surface properties, without affecting vesicle stability.

Thus vesicles or liposomes may be crosslinked either through the polar head groups or reactive groups within the hydrophobic membranes. Different head groups of vesicle-forming amphiphiles with vinyl substituents can be used in the invention. These groups can be polymerized on the outer surface with water-soluble initiators or on both surfaces with UV radiation. Reactive groups within the hydrophobic layer of the membrane are inaccessible to water-soluble reagents. In general, visible and UV radiation has been used to polymerize the amphiphiles through diene or diyne groups. The polymerization of diyne groups forms colored polyene-yne chains (Gros et al., 1981).

In one embodiment, liposome and vesicle bilayers can be mechanically stabilized by polymerization (Benita et al., 1996, p. 159; Boder et al., 1981), crosslinking or using lipids with fluorocarbon chains (Fuhrhop and Mathieu, 1984). In contrast to other vesicles or liposomes, the polymerizable ones cannot be as easily destroyed.

The core of the nano- and mesosized particles may contain an inorganic compound or a metal, or a combination thereof. The inorganic compound may be a metal oxide and/or hydroxide or a chalcogenide, e.g., a metal sulfide, selenide or telluride.

The metal of the organic compound may be an alkaline earth metal, a transition metal, a metal of Group 3A(13), 4A(14) or 5A(15) of the Periodic Table of Elements, or a combination thereof. Transition metals include Sc, Ti, V, Cr, Mn, Fe, Co, Ni, Cu, Zn, Y, Zr, Nb, Mo, Tc, Ru, Rh, Pd, Ag, Cd, Ba, La, Hf, Ta, W, Re, Os, Ir, Pt, Au, Hg and Ac. Alkaline earth metals include Mg, Ca, Sr and Ba. Group 3A(13) metallic elements include Al, Ga, In and Ti. Group 4A(14) metallic elements include Si, Ge, Sn and Pb. Group SA(15) metallic elements include As, Sb and Bi. In preferred embodiments, the metal of the metal oxide precursors is at least one of Al, Ti, Zr, Mg, Ca, Sr, Ba, or transition metals such as Zn, Cd, Fe, Ni, Co or the lanthanides. In more preferred embodiments, the metal is aluminum, titanium and zirconium In another preferred embodiment, the metal of the metal oxide precursors, metal organic compounds and inorganic salts is not silicon. In embodiments where two or more metals are present as the metal of the metal oxide precursors, metal organic compounds and inorganic salts, the first metal is one of those listed above and the second metal may be Al, Ti, Zr, Pd or Pt.

In one embodiment, the precursor of a metal oxide or hydroxide is a metal organic compound or an inorganic salt, wherein said organic compound is a metal alkoxide or metal carboxylate, and said inorganic salt is a metal halide or metal nitrate. Examples of metal alkoxides include alkoxides of straight or branched C1-C18 alcohols, optionally substituted by hydroxy, amino, oxo, and/or carboxylato such as, but not limited to, metal methoxides, metal ethoxides, metal propoxides, metal isopropoxides, metal butoxides, metal sec-butoxides, metal t-butoxides, metal ethylhexoxides, metal (triethanolaminato)isopropoxides, metal bis(ammonium lacto)dihydroxides, metal bis(ethyl acetoacetato)diisopropoxides, metal bis(2,4-pentanedionate) diiso-propoxides, and combinations of two or more of the above compounds. Metal carboxylates are derived from optionally substituted C1-C18 mono- or poly-carboxylic acids and include, but are not limited to, metal acetates, metal propionates, metal butyrates, metal ethylhexanoates, metal gluconates, metal oxalates, metal pantothenates, metal cyclohexanebutyrates, metal trifluoroacetyl-acetonates, metal citrates, and metal methacrylates. Inorganic salts include metal halides and metal nitrates. The precursor may also be a metal enolate derived from alpha-acylketones, such as aluminum acetylacetonate and zirconium acetyl acetonate, or the corresponding fluorinated derivatives of the metal enolates, such as a metal hexafluoroacetylacetonate. When silica is the desired core, the precursor may be tetraethyl orthosilicate.

In a preferred embodiment, the metal oxide precursor is a metal alkoxide. Specific examples of metal oxide precursors include, but are not limited to, aluminum triethoxide, aluminum isopropoxide, aluminum sec-butoxide, aluminum tri-t-butoxide, diethyl ethoxymagnesium malonate, zirconium ethoxide, zirconium isopropoxide, zirconium propoxide, zirconium butoxide, zirconium t-butoxide, zirconium acetate, titanium methoxide, titanium ethoxide, titanium isopropoxide, titanium propoxide, titanium butoxide, titanium bis (ethyl acetoacetato) diisopropoxide, titanium bis(2,4-pentanedionate)diisopropoxide, yttrium acetyl-acetonate, yttrium butoxide, yttrium hexafluoroacetylacetonate, yttrium isopropoxide, yttrium isopropoxide oxide, or combinations of two or more of the above compounds.

In addition, organometallic compounds that are soluble in a common solvent with the amphiphiles and may be used in the present invention are acetylacetonates, aliphatic, cycloaliphatic and aromatic carboxylates, and phenolates of nickel, cobalt, manganese, iron, copper, and zinc. Examples of such organometallic precursors include nickel acetylacetonate, cobalt acetylacetonate, manganese acetylacetonate, iron acetylacetonate, copper acetylacetonate, zinc acetylacetonate, Pd acetylacetonate, nickel naphthenate, cobalt naphthenate, manganese naphthenate, iron naphthenate, copper naphthenate, nickel 2-ethyl hexoate, cobalt 2-ethyl hexoate, manganese linolate, nickel stearate, manganese benzoate, iron benzoate, nickel 2,2'-sulfonyl bis(p-dodecylphenolate), cobalt 2,2'-sulfonyl bis(p-nonylphenolate), zinc 8-hydroxyquinolinate and the like. Other precursors that can be used are platinum acetylacetonate and palladium acetylacetonate and acetyl acetonates of chromium, molybdenum, tungsten, tin, Au, and Ag.

The acetylacetonato complex containing a metal is a complex having a metal atom coordinated with the anions acac produced from acetylacetone (2,4-pentadione) by acid dissociation, and is represented by the formula $(CH_3 COCH\text{-}COCH_3)_n$ M, wherein M represents a metal having a valence of n. In addition, other organometallic or other metal compound soluble in an organic solvent which are converted into insoluble oxides or hydroxides on exposure to water may be chosen from Groups 9 and 10 noble metal acetylacetonates and from Groups 14, 15, 16 and 17 of the Periodic Chart.

Representative organic metal-containing compounds which can be used to complex and solubilize the platinum group metals in organic solvents include ruthenocene, tricarbonyltris (triphenylphosphino) ruthenium, palladium acetylacetonate, tetrakis (triphenylphosphino) palladium, dichloro (ethylene) palladium (II) dimer, pi-cyclopentadinyldicarbonylosmium (I) dimer, platinum acetylacetonate, dichlorodicarbonylplatinum (II), trimethylplatinum chloride, dichlorotetracarbonyldirhodium (I), chlorocarbonylbis (tri-phenylphosphino) rhodium (I), triiodotricarbonyliridium (III), trichlorobis (trichlorophosphino) iridium (III) and the like.

The above organometallic precursors of the organometallics based on acetylacetonate, aliphatic, cycloaliphatic or aromatic carboxylate, and phenolate or metal compounds that are otherwise soluble in organic solvents but react with water to form water insoluble compounds may be used singly or in combination together with a given amphiphilic compound or a mixture of amphiphilic compounds with or without other compounds to help facilitate vesicle formation or subsequent treatment of the vesicles after they are formed. In order to recover the metal core from the organometallic complex, a mild reducing agent is added to the aqueous solution such as ascorbic acid, sulfide ions and the like.

According to the present invention, there are embodiments where only one type of inorganic or metal precursors is used so that particles comprising one type of inorganic or metal element or derivative encapsulated by the outer amphiphile are obtained. As shown in the examples hereinafter, nanoparticles comprising a core of silica, aluminum hydroxide/oxide, titanium oxide, zirconium oxide, palladium acetylacetonate and the like are obtained by encapsulation of the respective precursors. In other embodiments, mixtures of inorganic, organometallic or metallorganic compounds or complexes (such as metal acetylacetonates) are used as precursors so that the final product may be a nanoparticle comprising mixtures of metal oxides or hydroxides or metal oxides and hydroxides with dispersed metal particles. The dispersed metal particles are formed by the treatment of the metal precursor, e.g. metal complex, such that reducible compounds are reduced to the metal and are dispersed in those metal oxides or hydroxides that are not reduced. Thus, in one embodiment of the invention, the resulting nanoparticles are porous structures of a metal oxide such as silica, aluminum oxide, titanium oxide, zirconium oxide or ruthenium oxide with amounts of a metal such as Pd or Pt dispersed within the pores.

As shown hereinafter in the examples, the invention provides a method wherein the particles are made by dissolving an organometallic or metallorganic compound such as tetramethyl or tetraethyl orthosilicate, aluminum isopropoxide, titanium isopropoxide, titanium ethoxide or zirconium (IV) butoxide or a metal complex such as a Pd acetylacetonate and an amphiphile such as a phospholipid or a bolaamphiphile in a water-miscible common solvent such as isopropyl alcohol, injecting this solution under the surface of an aqueous solvent, whereby the amphiphile forms vesicles or liposomes encapsulating the precursor and wherein, within the encapsulated space of the vesicle or liposome, the organometallic, metallorganic or metal complex reacts with the water to form water-insoluble nano or mesosized-particles encapsulated within said vesicle or liposome. In one example, both Al isopropoxide and Pd acetylacetonate are used as precursors and the resulting core consists of porous nanopalticles of aluminum oxide or hydroxide with metallic Pd particles dispersed therein.

In addition to forming the water insoluble compounds from the above-mentioned precursors by their reaction with water, the precursors may react with ions such as sulfide ions dissolved in the water, for example sodium sulfide, in order to reduce any reducible solid compound obtained, if so desired.

In another embodiment, the core contains an inorganic chalcogenide of a transition metal. For example, the precursor $CuSO_4$ or Cu acetylacetonate may be encapsulated into the vesicle or liposoine and then reduced by sodium sulfide dissolved in the water to the chalcogenide CuS.

According to another embodiment of the present invention, it is envisaged to remove the amphiphile outer layer, after formation of the vesicles or liposomes, thus obtaining inorganic compound particles whose shape, morphology and density are controlled by the amphiphile layer. Thus, according to this embodiment, nano- and mesosized particles are obtained, which are primarily inorganic, with the organic amphiphile coating having been removed by one or more methods such as a chemical and/or thermal removal process for example.

The particles of the invention preferably have or approach a spherical shape. However, also particles having or approaching a cylindrical, tublet, fiber or ribbon shape are encompassed by the present invention. By the choice of suitable amphiphilic compounds, the shape of the submicron and nanometric organic-inorganic or inorganic particles is that of tublets, fibers, or ribbons. The choice of amphiphiles that will form a tublet, fiber, or ribbon configuration can be conducted as described in part in the following references: Schnur, 1993; Fuhrhop and Helfrich, 1993; and Fuhrhop and Wang, 2004.

In one embodiment, the particles obtained by the method of the invention are nanosized. In another embodiment, the particles have submicron dimensions. In a further embodiment, the particles have micron dimensions.

In one preferred embodiment of the invention, hollow vesicles of different shapes (spheres, oblate and prolate spheroids, fibers) and vesicle membrane permeability can be made by the choice of the suitable amphiphile and these vesicles can have high encapsulation efficiency. Thus, by injecting into an aqueous phase an alcoholic or ether solution mixture of a suitable precursor of an inorganic solid and a self-aggregating amphiphilic derivative, vesicles or liposomes are formed from the amphiphiles encapsulating the precursor. The subsequent process of precursor transformation to a solid inorganic particle via hydrolysis is controlled by the vesicle shape and membrane permeability, which in part controls the final shape, morphology and density of the nanoparticles. Thus the dissolved inorganic precursors hydrolyze while within the vesicle/liposomes, taking on the shape of the latter as well as their surface characteristics. The surface and/or bulk/volume characteristics can be controlled either by leaving the encapsulating amphiphilic membranes surrounding the inorganic particle, further treating this organic membrane by heat, pH or by chemical modification of the surface and/or bulk to strengthen or modify its permeability and or surface and/or bulk properties, or to remove the organic coating and expose the underlying surface of the inorganic particle.

Without being bound to any theory but only to indicate the scope of our invention, the following discussion on the parameters that affect the formation of the nanoparticles can illustrate the invention.

The parameters of the vesicle that can affect the final nanoparticle structure and material parameters (e.g., morphology, surface topology, surface charge, particle density and internal porosity and pore size, etc) can be related to: (i) the amphiphile molecular structure and the self-aggregating structures that they form; (ii) the operations involved in the vesicle formation; (iii) the nature of the solvent external to the interior of the vesicle, which is, in most cases, an aqueous solution; (iv) the properties of the initial solvent within the vesicles; and (v) the characteristics of the inorganic precursor such as the mechanism and kinetics of transformation into solid particles.

Regarding the parameter (i), some particular examples are the effect of the amphiphile head group that may be cationic (e.g., quaternary ammonium), anionic (e.g., sulfonic, carboxylic, phosphonic, etc), noncharged neutral (e.g., glucoside moieties, polyethylene glycol (PEG), polypropylene oxide, etc), or amphiphilic (e.g., phosphatidylcholine, phosphatidylserine, etc) and its interaction with the inorganic precursor. The mechanism and kinetics of the transformation of the precursors into a solid particle can be significantly influenced by the interaction of the head groups facing the interior of the vesicle and thus in contact with the precursor and can influence the precursor or entities formed along the stages of said transformation. In addition, this interaction can also influence final surface properties as well as shape, morphology, density and pore size within the final particle. The shape of the vesicle that encapsulates the inorganic particle precursor may also influence the final particle pore size.

In another embodiment, mixtures of different amphiphiles may be used so that different head groups or aliphatic chains may be present to modify vesicle forming properties, or formation conditions or interaction with the inorganic precursor or ultimate inorganic materials or final vesicle performance characteristics. For example, the head groups may be an anionic head group such as carboxylic acid or sulfonic acid and a neutral head group such as PEG. In addition, additives, e.g., cholesterol and cholesterol derivatives, which are well known to modify vesicle membrane characteristic such as mechanical strength and cohesiveness, may be added to the amphiphile mixtures.

In another mode of influencing the final structural characteristics of the amphiphile, the vesicle membrane can be used to control the permeation of water, solvent and organic entities in and out of the vesicles. In this way, the kinetics of precursor transformation from the original dissolved solute is controlled and this will influence final surface properties as well as shape, morphology density and pore size within the final particle.

Many new technologies are being developed based on submicron inorganic or inorganic-organic hybrid entities such as particles of irregular, ellipsoidal, spherical, fiber, or ribbon shape. For example, the following applications may use submicron or nano-sized particles in their final product: inks for ink jet printers, filter devices such as for nanofiltration (NF) and reverse osmosis (RO), porous catalysts in which the substrate flows through, dense or porous catalytic particles that should be homogeneously dispersed into a solution, fillers for polymer composite materials, or components of alloys or particles used for transport in and through biological compartments for the purpose of diagnosis or delivery of active agents by a passive or active delivery mechanism. To take advantage of the properties that said particles can contribute to these and other applications, requires that they be manufactured in non-aggregated forms, and that in the processing into the final product they are initially separated or easily separated from each other, and/or that they can be mixed uniformly into a solution or paste, and/or that they can be controllably ordered into ordered macro structures.

Submicron sized inorganic or inorganic-organic hybrid particles, however, especially in the nano range, are difficult to make and difficult to process into their final shape or mix into homogenous solutions or blends without aggregation. The reason is that small sized particles have high surface areas resulting in a tendency for aggregation to reduce the high interfacial energies with the surroundings. Such particles are thus difficult to manufacture cost effectively in non-aggregate form, and even more difficult in many applications to process them into their final solid products or solution or melt suspensions. One of the advantages of the present invention is that nanoparticle aggregation is minimized or eliminated.

In one preferred method used according to the invention, an amphiphile alcohol solution is injected through a fine needle into an excess solution of saline or other aqueous media. The force of injection is usually sufficient to achieve complete mixing so that the alcohol is diluted almost instantaneously in water and the lipid molecules are dispersed evenly throughout the media. As a function of the amphiphile structure, this procedure gives a high percentage of small unilamellar vesicles (SUV; ~25 nm diameter) although larger vesicles may form at lower mixing rates (see Roger, 1990; chapter 2 and the references in that chapter). In the present invention, the alcohol solution of the lipid will also contain a precursor to the nanoparticle, which forms the insoluble core in the water solution. The insoluble core may be formed due to a hydrolysis reaction, which forms an insoluble metal hydroxide or oxide, or may be due to the presence of hydroxyl groups, which form an insoluble hydroxide from a metal complex.

Vesicles made from phospholipids and other amphiphilic compounds which form bilayer membranes, may be characterized as small unilamellar vesicles which are 200-500 Å in diameter (SUV), or large unilamellar (single) bilayer layer vesicles characteristically 0.1 to 10 microns in diameter (LUV), or multilamellar vesicles of 1000 Å to 8000 Å in diameter (MLV).

One important aspect of the invention is that hollow vesicles of different shapes (spheres, tublets, fibers) and vesicle membrane permeability can be made by the choice of the amphiphile. These amphiphiles can organize into vesicles whose structure is a function of the choice of amphiphile and the conditions of vesicle formation. A preferred approach consists in injecting into an aqueous phase an alcoholic or ether solution mixture of a precursor to an inorganic solid and a self-aggregating amphiphilic derivative, whereby vesicles or liposonies are formed from the amphiphiles encapsulating the precursor. The subsequent process of transformation of the precursor into a solid inorganic particle via hydrolysis is controlled by the vesicle shape and membrane permeability, which in part controls the final shape, morphology and density of the nanoparticles. Thus the inorganic precursors hydrolyze within the vesicle/liposomes taking on the shape of the latter as well as the surface characteristics.

The vesicles of the invention are hybrid organic-inorganic materials composed of an organic amphiphilic component, which aggregates into a spherical or cylindrical membrane encapsulating a core. This core may be chosen from inorganic materials such as oxide, hydroxides, chalcogenides, metals and ceramics, e.g., rare earth oxides, ferric oxide, titanium oxide, gold, platinum, palladium, and the like. The inorganic core may be solid or porous and may act as a matrix for organic or inorganic drug molecules whose release may be controlled upon external excitation of the matrix.

After vesicle formation, the cores of the vesicles are no longer soluble in the solvents in which they were fabricated. Similarly, the encapsulated organic membrane can also be insolubilized, if necessary. The surface of the vesicles is ionically charged in order to prevent aggregation and may also be made with steric blockers such as PEG (polyethylene glycol) protruding from the surface.

The dielectric constant of the encapsulated core in some embodiments can take on values of its inorganic core which may vary from between 2 to 10 to 20 (magnesium titanate) to as high as 2000 for a barium titanate core. Alternatively, the core may contain metals and their derivatives, which are magnetic, e.g. $Fe_2O_3$.

The nano- and mesosized particles of the present invention can be used in many applications, for example, for high resolution ink jet printing, porous macroscopic structures for catalysis, nano-scale electronic devices, medical diagnostics and therapy and the formation of thin film composites for water application. In particular, some preferred, but non-limiting applications, include using the nano particles as catalytic electrodes in fuel cells and energy storage devices. Another important application is in drug delivery. The nanoparticles with a porous solid core, preferably of low density, or a hollow vesicle or liposome comprising inorganic porous cores may contain biologically active molecules and may be used for drug delivery, disease treatment and/or diagnostics as described, for example, in U.S. Pat. Nos. 5,389,377 and 5,441,746 and US Patent Application 2002/0103517, which are incorporated here by reference. Examples of drugs or active agents which may be delivered are: terbutaline, albuterol, stropine methyl nitrate, cromolyn sodium, propracalol, funoisolide, ibuprofin, geniamycin, tobermycin, pentamidine, penicillin, theophylline, bleomycin, etopoxide, captoprel, n-acetyl cysteine, verapamil, vitamins, and radioopaque and particle-emitter agents, such as chelated metals. A second general class of drugs is peptide or protein molecules, such as peptide hormones, enzymes, enzyme inhibitors, apolipoproteins, and high molecular weight carbohydrates. Representative compounds in this class include calcitonin, atriopeptin, alpha.-1 antitrypsin (protease inhibitor), interferons, oxytocin, vasopressin, insulin, interleukin-2, superoxide dismutase, tissue plasminogen activator (TPA), plasma factor 8, epidermal growth factor, tumor necrosis factor, lung surfactant protein, lipocortin, macrophage colony stimulating factor, and erythropoietin. A third class of drugs are lipophilic molecules including prostaglandins, amphotericin B, progesterone, isosorbide dinitrate, testosterone, nitroglycerin, estradiol, doxorubicin, epirubicin, beclomethasone and esters, vitamin E, cortisone, dexamethasone and esters, and betamethasone valerete.

In another application, the inorganic core liposome composition is designed for targeting a specific target tissue or organ, by having anchored surface ligands with selective sites for it to bind to moieties on the target site. This feature allows for targeting a tumor tissue, for drug treatment by, for example, intravenous administration to a tumor-bearing subject. As another example, the inorganic core liposomes may be prepared with surface-bound ligand molecules, such as antibodies, which are effective to bind specifically and with high affinity to ligand-binding molecules such as antigens, which are localized specifically on target cells. A variety of methods for coupling ligands to the surface of liposomes are known, including the incorporation of ligand-derivatized lipid components into liposomes or coupling of ligands to activated liposome surface components.

The targeted inorganic core liposomes may be prepared to include cancer chemotherapeutic agents, such as those listed above. In one preferred embodiment, the liposomes or vesicles of this invention are prepared to include PEG-PE and PG, to a final concentration of charged lipids or amphiphile up to 40 mole percent, doxorubicin or a taxol derivative, and remainder neutral phospholipids or neutral phospholipids and cholesterol.

In an inorganic core liposome or vesicle composition, which is useful for radio-imaging of solid tumor regions, the liposomes are prepared with encapsulated radio-opaque or particle-emission metal, typically in a chelated form, which substantially prevents permeation through the vesicle or liposome bilayer.

One important application of the nanovesicles of the invention consists in adding thereto surface ligands that target to antigens at a diseased tissue.

Imaging is another important application for the nanovesicles of the invention. For example, as an MRI agent targeted to fibrin for cardiovascular MRI, and in another case that targets a key hallmark of cancer, alpha v beta 3, an angiogenesis biomarker, and uses it as a targeting ligand. The probes may not only be markers but they may also deliver active agents. For example, it could be a biomarker for cancer that is also able to deliver a chemotherapeutic to the tumor site. The drug carrier/sensor system integrates the features of monitoring and controlling drug delivery into a nanosize single unit that function both as sensor and drug delivery system.

In still another application, the vesicle/liposome composition can enhance uptake of circulating cells or other blood-borne particles, such as bacteria, virus-infected blood cells and the like. Here, the long-life vesicles/liposomes are prepared to include surface-bound ligand molecules, as above, which bind specifically and with high affinity to the selected blood-borne cells. Once bound to the blood-borne particles, the vesicle/liposomes can enhance uptake by the RES.

In one embodiment, the hybrid vesicles are capable of penetrating the blood-brain-barrier (BBB) due to the presence of surface groups that facilitate passage through the BBB. These surface groups may be BBB permeabilizers, such as the bradykinin B2 agonist, RMP-7, which are transported across the BBB via specific transporters and have been employed in the design of prodrugs that penetrate the BBB [Yang et al., 2001], or OX26 monoclonal antibody to the rat transferrin receptor that has been used for the delivery of liposome to the brain.

The invention will now be illustrated by the following non-limiting Examples.

EXAMPLES

Example 1

Preparation of Liposomes Encapsulating Aluminum Hydroxide by the 'Ethanol Injection' Method In the following Examples 1 to 6, the so-called method of "ethanol injection" was used, but with isopropyl alcohol as the common solvent.

Diphthaloyl phosphatidylcholine (DPPC; 20 mg) and aluminum isopropoxide (21.6 mg) were dissolved in 0.5 ml isopropyl alcohol (lipid solution). One ml of nitrogen-purged aqueous media (e.g. water, saline, solute solution, etc) was placed in a 5 ml vial and stirred rapidly using a magnetic stirrer. A fine gauge needle was fitted to a 1 ml glass syringe and used to draw up to 100 µl of the lipid solution. The tip of the needle was positioned below the surface of the stirred aqueous solution, said solution was kept above the critical temperature (Tc) of the DPPC, at 55° C., and the lipid solution was injected as rapidly as possible into the aqueous media, while it was kept at 55° C. Liposomes were formed immediately with encapsulated aluminum hydroxide precursor, which converts to its water-insoluble product aluminum hydroxyde or oxide within the liposome.

The solution was allowed to cool to room temperature. The liposomes can then be further concentrated and purified from the alcohol by an ultrafiltration (UF) membrane at low pressure (10 psi) in an Amicon concentrator using an XM-100 Å membrane at rapid stirring rate. The isopropyl alcohol may also be removed from the bulk medium by dialysis or diafiltration. The resulting nanoparticles were suspended without aggregation having average diameter of about 30 ml with good homogeneity. The suspension was stable without apparent aggregation or precipitates.

When this example was repeated without the presence of DPPC, the resulting particles were very small (~10 nm) and aggregated without uniformity.

Example 2

Preparation of Liposomes Encapsulating Silica by the 'Ethanol Injection' Method

Example 1 was repeated using tetraethyl orthosilicate (TEOS) instead of aluminum isopropoxide, at the same concentration. The resulting nanoparticles containing insoluble silica in the core were about 45 nm diameter on average with good homogeneity. The suspension was stable without apparent aggregation or precipitates. When this example was repeated without DPPC, the resulting particles were very small and aggregated without uniformity.

Example 3

Preparation of Vernonia Oil Vesicles Encapsulating Aluminum Hydroxide by the 'Ethanol Injection' Method Example 1 was repeated, but using the quaternary amphiphilic derivative of vernonia oil (VOquat DMDoA Cl, $C_{105}H_{200}O_{15}N_3Cl_3$ (M.W.=1849.7) prepared as described in WO 02/055011, instead of DPPC. 20.7 mg of the quaternary derivative of vernonia oil and 17.7 mg of aluminum isopropoxide were dissolved in 0.5 ml isopropyl alcohol. The process was continued similarly to the description in Example 1, but at room temperature (and not at 55° C.), resulting in nanoparticles of aluminum oxide or hydroxide core encapsulated in a membrane of vernonia oil quaternary derivative, with average diameter of about 80 nm and good homogeneity. The suspension was stable without apparent aggregation or precipitates.

When this example was repeated without the vernonia oil derivative, the resulting particles were aggregated and non-uniform.

Example 4

Preparation of Vernonia Oil Vesicles Encapsulating Silica by the 'Ethanol Injection' Method Example 3 was repeated using 31.2 mg tetraethyl orthosilicate instead of aluminum isopropoxide. The resulting nanoparticles with an insoluble silica derivative in the core of the vesicles were about 38 nm in diameter on average with good homogeneity. The suspension was stable without apparent aggregation or precipitates. When this example was repeated without the vernonia oil derivative, the resulting particles were aggregated and non-uniform.

Example 5

Preparation of Vernonia Oil Vesicles Encapsulating Titanium Oxide by the 'Ethanol Injection' Method Example 3 was repeated using 25.5 mg titanium ethoxide instead of aluminum isopropoxide. The resulting nanoparticles with an insoluble titanium oxide or hydroxide derivative in the core of the vesicles were about 60 nm in diameter on average with good homogeneity. The suspension was stable without apparent aggregation or precipitates. When this example was repeated without the presence of the vernonia oil derivative, the resulting particles were aggregated and non-uniform.

Example 6

Preparation of Vernonia Oil Vesicles Encapsulating Zirconium Derivative by the 'Ethanol Injection' Method Example 3 was repeated using 21.8 mg zirconium butoxide instead of aluminum isopropoxide. The resulting nanoparticles with an insoluble zirconium derivative in the core of the vesicles were about 40 nm in diameter on average with good homogeneity. The suspension was stable without apparent aggregation or precipitates. When this example was repeated without the presence of the vernonia oil derivative, the resulting particles were aggregated and non-uniform.

Example 7

Preparation of Vernonia Oil Vesicles Encapsulating Silica by the Film Formation Method and Hydration Instead of the method of ethanol injection, the nanovesicles with the inorganic oxide or hydroxide core were made by the process of film formation followed by hydration and, optionally, sonication. This process involves evaporating the organic solvent from a solution of the material forming the liposome or vesicle membrane with the organometallic or metallorganic or complex compounds under vacuum to form a thin film on the inner surface of a round-bottomed flask, then adding an aqueous solution to hydrate the film, followed by sonication to form the vesicles or liposomes which encapsulate the nanoparticles.

In the present example, 34 mg of the vernonia oil derivative VO quat used in Example 3 were dissolved together with 17.7 mg tetraethyl orthosilicate (10.29% in the lipid) in 5 ml of a 1:2 mixture of methanol and methylene chloride. The solution was placed in a 50 ml round bottom flask and dried to a thin film under vacuum at 50° C. for 60 minutes, and then at 50° C. for 30 minutes without vacuum. To this film, 5 ml of de-ionized water was added, followed by 30 min in the ultrasonic bath at room temperature. The concentration of the lipid in the water was finally 0.992%. The resulting particles were about 120 nm in diameter and the solution was stable without apparent aggregation or precipitates.

In variations of the above, the dried film prior to hydration is kept under vacuum for more than 60 minutes and up to overnight instead of 60 minutes, in order to remove all residual solvents, and without the step of 50° C. for 30 minutes without vacuum.

Example 8

Preparation of Vernonia Oil Vesicles Encapsulating Aluminum Oxide/Hydroxide by the Film Formation Method and Hydration Example 7 was repeated using 8.4 mg of aluminum isopropoxide instead of tetraethyl orthosilicate, which is 8.94% in the lipid, and 20 mg of the VO quat derivative of vernonia oil described in Example 3 (VO quat concentration in water was 1.175%). Two ml of water were used for hydration instead of the 5 ml in 7c. The average diameter of the resulting nanoparticles was about 95 nm. The suspension was stable without apparent aggregation or precipitates

Example 9

Preparation of vernonia oil vesicles encapsulating titanium oxide by the film formation method and hydration Example 7 was repeated using 13.3 mg of titanium ethoxide (instead of tetraethyl orthosilicate), which was 20.16% in the lipid, and instead of 5 ml of water, 2 ml of water were used, wherein the VO quat concentration in the water was 1.155%. The resulting nanoparticles were about 160 nm in diameter on average with good homogeneity and the solution was stable without apparent aggregation or precipitates.

Example 10

Preparation of Vernonia Oil Vesicles Encapsulating Zirconium Oxide by the Film Formation Method and Hydration Example 7 was repeated using 10.6 mg of zirconium butoxide (instead of tetraethyl orthosilicate), which was 11.54% in the lipid, and 2 ml of water were used wherein the VO quat concentration in the water was 1.18% (25 mg). The resulting nanoparticles were 130 nm in diameter on average and the solution was stable without apparent aggregation or precipitates.

Example 11

Preparation of Liposomes Encapsulating Zirconium Oxide by the Film Formation Method and Hydration Example 10 was repeated using 10.6 mg of zirconium butoxide, 20 mg of distearoyl phosphatidylcholine and 10 mg cholesterol with good results. The aqueous solution was kept at 65° C. (which is 5° C. above the Tc of the lipid) until after all the organic solution was injected and then allowed to slowly cool to room temperature. The resulting nanoparticles were 58 nm in diameter on average and the suspension was stable without apparent aggregation or precipitates.

Example 12

Preparation of Vernonia Oil Vesicles Encapsulating Aluminum Oxide by the Injection Method Example 3 was repeated using ethyl ether instead of ethanol. The ether solution of aluminum isopropoxide and the amphiphile was injected into a stirred solution placed in a water bath at 40° C. The average diameter of the resulting particles was below 100 nm and the suspension was stable without apparent aggregation or precipitates.

Example 13

Preparation of Vernonia Oil Vesicles Encapsulating Aluminum Oxide by the Ethanol Injection Method Example 3 was repeated using 15 mg of aluminum isopropoxide and 18 mg of the symmetric bola-amphiphile N,N'-ethylene bis(vernolamide) (instead of the VO quat DMDoA Cl derivative). The bola-amphiphile was prepared from methyl ester of [octadec-9-en-12(13)-hydroxy, 13(12)-(oxy-carbonyl-N-methylene-N,N-dimethyl-N-dodecylammonium chloride) methanoate as described in WO 02/055011. The average size of the resulting nanoparticles was 40 nm diameter with good uniformity. The suspension was stable without apparent aggregation or precipitates.

Example 14

Preparation of Liposonies Encapsulating Aluminum Oxide by the 'Ethanol Injection' Method Example 3 was repeated using the racemic mixture of 1,2-bis(tricosa-10,12-diynoyl)-sn-glycero-3-phosphocholine (described by Schnur, 1993), instead of the vernonia oil derivative VO quat DMDoA Cl. The resulting particles containing the aluminum oxide core had a cylindrical shape with an outer average diameter of about 100 nm, rather than a spherical shape as seen in other examples using other derivatives.

Example 15

Preparation of Liposomes Encapsulating Pd Acetylacetonate by the 'Ethanol Injection' Method Example 1 was repeated using 16 mg of palladium acetylacetonate instead of aluminum isopropoxide. The resultant microcapsules contained a core of water-insoluble palladium acetylacetonate. Addition of a reducing agent will result in particles with a Pd core.

Example 16

Preparation of Nanoparticles of Aluminum Hydroxide/Oxide with Metal Pd Particles Dispersed Therein Example 1 was repeated using a mixture of aluminum isopropoxide and palladium acetylacetonate. Twenty mg of diphthaloyl phosphatidylcholine, 21.6 mg of aluminum isopropoxide and 5 mg of palladium acetylacetonate were dissolved in 0.8 ml isopropyl alcohol. The resultant microcapsules contained a core of aluminum hydroxide or oxide and palladium acetylacetonate. The palladium acetylacetonate was further reduced to palladium metal to give a porous nano particle of aluminum hydroxide or oxide, containing metallic Pd particles dispersed within.

REFERENCES

Batzri S, and Korn E. D., Single bilayer liposomes prepared without sonication, Biochim. Biophys. Acta, 298, 1015, 1973.

Benita S., (editor), Microencapsulation Methods and Industrial Applications, Marcel Dekker, Inc., 1996.

Boder H., Ringdorf H. and Skura, J., Liposomes from Polymerizable Glycolipids, *Angew. Chem. Int. Ed. Engl,* 20, 91-92,1981.

Deamer, Preparation and properties of ether-injection liposomes, Ann. N.Y. Acad. Sci., 308, 250-258, 1978.

Fuhrhop J. H. and Mathieu J., Routes to Functional Vesicle Membranes without Proteins, *Angew. Chem. Int. Ed. Engl.* 23, 100-113, 1984.

Fuhrhop J. H and Helfrich W., Fluid and Solid Fibers Made of Lipid Molecular Bilayers, *Chem. Rev.,* 93, 1565-1582, 1993.

Fuhrhop J. H and Wang T., Bolaamphiphiles, *Chem. Rev.,* 104, 2901-2937, 2004.

Gros L., Ringsdorf., H and Schupp H., *Angew. Chem. Int. Ed. Engl,* 93, 511, 1981.

Kiatagiri K., Hamasaki R., Ariga K. and Kikuchi J. I., Preparation and Surface Modification of Novel Vesicular Nanoparticle, J. Sol-Gel Sci. Techn. 26, 393-396, 2003.

Kunitake T., Okahata Y. J., Shimomura M., Yasunami S., Formation of Stable Bilayer Assemblies in Water from Single Chain Amphiphiles. Relationship between the Amphiphiles Structure and Aggregate Morphology, *J. Am. Chem Soc.,* 103, 5401-5413, 1981.

Hentze H. P., Raghavant S. R., McKelvey C. A., and Kaler E. W., Silica hollow spheres by templating of catanionic vesicles. *Langmuir,* 19, 1014-1069, 2003.

Jung J. H., Ono H., Sakurai K., Sano M. and Shinkai S., Novel Vesicular Aggregates of Crown-Appended Cholesterol Derivatives which Act as Gelators of Organic Solvents and as Templates for Silica Transcription", *J. Am. Chem. Soc.,* 122, 8648-8653, 2000.

Roger R. C. (Ed.), "Liposomes, A Practical Approach", New Oxford Press, 1990.

Schnur J. M., "Lipid Tubules: A Paradigm for Molecularly Engineered Structures", *Science,* 262, 1669-1675, 1993.

Sumida Y., Masuyama A., Kida Y., Nakatsuji I., Ikeda I. and Nojima M., New pH-sensitive vesicles, release control of trapped materials from the inner aqueous phase of the vesicle made from triple-chain amphiphiles bearing two carboxyl groups, *Langmuir,* 17, 609-612, 2001.

Tanevt P. T. and Pinnavaia T. J., Biomimetic assembly of porous lamellar silica molecular sieves with a vesicular particle architecture. *Supramolecular Science,* 5, 399-404, 1998.

Torchilin V. and Weissig V. (eds), Liposomes—A Practical Approach, $2^{nd}$ Ed., Oxford Press, 2003.

Yang C. et al. Prodrug-based optimal drug delivery via membrane transporters. Expert Opin. Biol. Ther. 1(2): 159-175, 2001.

The invention claimed is:

1. Method for the preparation of nano- and mesosized particles consisting of a lipid layer comprising at least one amphiphile and a core of a metal oxide or hydroxide, said method comprising: (i) dissolving in a common solvent at least one self-aggregating amphiphile with at least one inorganic, organometallic or metallorganic precursor of said inorganic compound or metal; and (ii) either injecting the resulting solution into an aqueous solution or drying the resulting solution and re-hydrating it, so as to form in both cases nano- and mesosized particles in which the precursor is encapsulated by the amphiphile(s) and is converted therein to said inorganic compound and/or metallic solid form wherein said precursor is a metal alkoxide; and wherein said precursor which is encapsulated is converted to said metal oxide or hydroxide by contact with a reducing agent.

2. A method according to claim 1, wherein said particles are selected from nano- and mesosized vesicles, liposomes and tubular particles.

3. A method according to claim 2, wherein the at least one amphiphile is chosen from compounds which form monolayer, bilayer or multilamellar vesicles or liposomes.

4. A method according to claim 3, wherein said at least one amphiphile is a symmetric or asymmetric bolaamphiphile that forms monolayer vesicles or liposomes.

5. A method according to claim 3, wherein said at least one amphiphile is an amphiphile containing one or more aliphatic or aliphatic-aromatic chains and one or more headgroups with a packing geometry that allows formation of bilayer or multilamellar vesicles or liposomes.

6. A method according to claim 3, wherein said at least one amphiphile does not have the packing geometry that allows formation of bilayer or multilamellar vesicles or liposomes and this ability is provided by: (i) addition of cholesterol; or (ii) addition of an additional amphiphile that imparts to the first amphiphile the capability of formation of bilayer or multilamellar vesicles or liposomes.

7. A method according to claim 3, wherein said amphiphile can undergo polymerization and/or cross-linking.

8. A method according to claim 2, wherein said at least one amphiphile is a combination of two amphiphiles in which one forms monolayer and the other forms bilayer or multilamellar vesicles or liposomes.

9. A method according to claim 1, wherein said core contains an inorganic oxide and/or hydroxide of an alkaline earth metal, a transition metal, a metal of Group 3A(13), 4A(14) or 5A(15) of the Periodic Table of Elements, or a combination thereof.

10. A method according to claim 1, further comprising removing the amphiphile outer layer thus obtaining inorganic compound particles whose shape, morphology and density are controlled by the amphiphile layer.

11. A method according to claim 1, wherein the particles have or approach a spherical shape.

12. A method according to claim 1, wherein the particles have or approach a cylindrical, fiber or ribbon shape.

13. A method according to claim 1, wherein the particles are nanosized.

14. A method according to claim 1, wherein the particles have submicron dimensions.

15. A method according to claim 1, wherein the particles have micron dimensions.

16. A method according to claim 2, wherein the membrane or film of the vesicle or liposome prevents aggregation of the formed inorganic particles.

17. A method according to claim 1, wherein the nano- or mesosized particles undergo further chemical or thermal treatment.

* * * * *